United States Patent
Moyer et al.

(10) Patent No.: US 11,540,883 B2
(45) Date of Patent: Jan. 3, 2023

(54) VIRTUAL REALITY TRAINING FOR MEDICAL EVENTS

(71) Applicant: THOMAS JEFFERSON UNIVERSITY, Philadelphia, PA (US)

(72) Inventors: Timothy G. Moyer, Philadelphia, PA (US); Pavitra Krishnamani, Hockessin, DE (US); Corey B. Fischer, Philadelphia, PA (US); Daniel Holmes, Philadelphia, PA (US); Tejal Naik, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 54 days.

(21) Appl. No.: 16/813,259

(22) Filed: Mar. 9, 2020

(65) Prior Publication Data
US 2020/0281657 A1    Sep. 10, 2020

Related U.S. Application Data

(60) Provisional application No. 62/815,821, filed on Mar. 8, 2019.

(51) Int. Cl.
| | |
|---|---|
| *A61B 34/10* | (2016.01) |
| *A61B 90/00* | (2016.01) |
| *G06T 19/00* | (2011.01) |
| *G02B 27/01* | (2006.01) |
| *G06F 3/16* | (2006.01) |
| *G09B 9/00* | (2006.01) |
| *G10L 13/08* | (2013.01) |

(52) U.S. Cl.
CPC ............. *A61B 34/10* (2016.02); *A61B 90/36* (2016.02); *G02B 27/0172* (2013.01); *G06F 3/167* (2013.01); *G06T 19/006* (2013.01); *G09B 9/00* (2013.01); *G10L 13/08* (2013.01); *A61B 2090/365* (2016.02)

(58) Field of Classification Search
CPC ....................................................... A61B 34/10
USPC ............................................. 703/11; 345/633
See application file for complete search history.

(56) References Cited

U.S. PATENT DOCUMENTS

| | | | |
|---|---|---|---|
| 8,932,063 B2 * | 1/2015 | Taylor | G09B 23/28 219/617 |
| 10,490,191 B1 * | 11/2019 | Benkreira | G10L 15/22 |

(Continued)

OTHER PUBLICATIONS

Hayes, et al., "Residents feel unprepared and unsupervised as leaders of cardiac arrest teams in teaching hospitals: A survey of internal medicine residents", Critical Care Medicine; 35(7); doi:10.1097/01.ccm.0000268059.42429.39, 2007, 1668-1672.

*Primary Examiner* — Javid A Amini
(74) *Attorney, Agent, or Firm* — Saul Ewing Arnstein & Lehr LLP; Kathryn Doyle; Mark D. Simpson

(57) ABSTRACT

Systems and methods for virtual reality (VR) training of medical events are described herein. In one aspect, a method for generating a VR medical training environment can include displaying a medical event through a VR headset, receiving, from a user of the VR headset, a set of verbal responses corresponding to the user reacting to the medical event, determining a timestamp for at least one verbal response received from the user, determining a medical event score for the user based on the set of verbal responses and the timestamp, and displaying a summary of the medical event score via the VR headset or a display screen.

13 Claims, 3 Drawing Sheets

(56) References Cited

U.S. PATENT DOCUMENTS

| | | | | |
|---|---|---|---|---|
| 10,492,981 B1* | 12/2019 | Kumar | | A61H 19/44 |
| 10,600,335 B1* | 3/2020 | Donovan | | H04L 67/1057 |
| 11,113,987 B1* | 9/2021 | Jaggers | | G06Q 10/06311 |
| 2002/0150966 A1* | 10/2002 | Muraca | | G01N 33/5088 |
| | | | | 702/19 |
| 2003/0031992 A1* | 2/2003 | Laferriere | | H04L 69/329 |
| | | | | 434/262 |
| 2004/0024288 A1* | 2/2004 | Uchikubo | | A61B 1/0005 |
| | | | | 600/101 |
| 2004/0085443 A1* | 5/2004 | Kallioniemi | | G06V 20/693 |
| | | | | 348/135 |
| 2009/0202972 A1* | 8/2009 | Adhami | | G09B 23/28 |
| | | | | 434/362 |
| 2011/0224574 A1* | 9/2011 | Sadler | | G01N 33/5091 |
| | | | | 600/562 |
| 2011/0234782 A1* | 9/2011 | Ehrhardt | | A61B 1/0684 |
| | | | | 362/574 |
| 2012/0156712 A1* | 6/2012 | Takats | | G01N 1/02 |
| | | | | 435/287.1 |
| 2012/0274631 A1* | 11/2012 | Friedland | | G06T 19/20 |
| | | | | 606/280 |
| 2013/0296908 A1* | 11/2013 | Schulte | | A61B 18/1206 |
| | | | | 606/169 |
| 2014/0005483 A1* | 1/2014 | Ohashi | | A61B 1/0646 |
| | | | | 600/162 |
| 2014/0081659 A1* | 3/2014 | Nawana | | A61B 5/4833 |
| | | | | 705/3 |
| 2014/0188133 A1* | 7/2014 | Misener | | A61B 8/0841 |
| | | | | 606/130 |
| 2015/0248793 A1* | 9/2015 | Abovitz | | G02B 27/42 |
| | | | | 345/633 |
| 2016/0100763 A1* | 4/2016 | Fengler | | A61B 1/00186 |
| | | | | 600/473 |
| 2016/0167672 A1* | 6/2016 | Krueger | | G06V 40/19 |
| | | | | 340/576 |
| 2016/0174848 A1* | 6/2016 | Ammar | | A61B 1/00009 |
| | | | | 600/476 |
| 2016/0317383 A1* | 11/2016 | Stanfield | | A61H 3/061 |
| 2016/0328522 A1* | 11/2016 | Howley | | G06F 3/0482 |
| 2017/0039423 A1* | 2/2017 | Cork | | A61B 1/00055 |
| 2017/0148073 A1* | 5/2017 | Nomula | | G06Q 30/0617 |
| 2017/0213473 A1* | 7/2017 | Ribeira | | G16H 40/67 |
| 2017/0221484 A1* | 8/2017 | Poltorak | | G06K 9/00302 |
| 2018/0286272 A1* | 10/2018 | McDermott | | G09B 5/02 |
| 2018/0308339 A1* | 10/2018 | Marra | | G08B 5/36 |
| 2019/0000578 A1* | 1/2019 | Yu | | A61B 34/10 |
| 2019/0005838 A1* | 1/2019 | Yu | | G06F 3/011 |
| 2019/0005848 A1* | 1/2019 | Garcia Kilroy | | G06T 3/40 |
| 2019/0035385 A1* | 1/2019 | Lawson | | G10L 15/063 |
| 2019/0043214 A1* | 2/2019 | Chilcote-Bacco | | G06T 19/00 |
| 2019/0090969 A1* | 3/2019 | Jarc | | G16H 40/67 |
| 2019/0133689 A1* | 5/2019 | Johnson | | A61B 34/10 |
| 2019/0180637 A1* | 6/2019 | Mealer | | G06F 3/014 |
| 2019/0282324 A1* | 9/2019 | Freeman | | A61M 16/0084 |
| 2020/0133629 A1* | 4/2020 | Pratt | | H04L 67/12 |
| 2020/0175971 A1* | 6/2020 | Arora | | G10L 13/00 |
| 2020/0193264 A1* | 6/2020 | Zavesky | | G06N 20/00 |
| 2020/0342403 A1* | 10/2020 | Woolford | | G06Q 10/10 |
| 2021/0020060 A1* | 1/2021 | Hirsch | | G06F 3/011 |
| 2021/0065896 A1* | 3/2021 | Chiu | | G06T 19/006 |

* cited by examiner

200

VIRTUAL REALITY TRAINING FOR MEDICAL EVENTS

CROSS-REFERENCE TO RELATED APPLICATIONS

This application claims priority to U.S. Provisional Patent Application No. 62/815,821, filed Mar. 8, 2019, which is incorporated herein by reference in its entirety.

BACKGROUND OF THE INVENTION

Medical professionals spend a significant amount of time educating themselves on information prevalent to their medical field as well as maintaining their preparedness for certain medical events that they may possibly encounter. In some cases, medical professionals may educate and train themselves to prepare for certain "codes" they may experience. For example, medical professionals may train for Advanced Cardiac Life Support (ACLS) event codes, where a patient may experience a cardiac arrest. However, while medical professionals train to mitigate these code events, in some cases these medical professionals may find it difficult to experience team leading and communication management scenarios that are required for effectively combating emergency medical events such as code events.

SUMMARY

Systems and methods for virtual reality (VR) training of medical events are described herein. In one aspect, a method for generating a VR medical training environment can include displaying a medical event through a VR headset, receiving, from a user of the VR headset, a set of verbal responses corresponding to the user reacting to the medical event, determining a timestamp for at least one verbal response received from the user, determining a medical event score for the user based on the set of verbal responses and the timestamp, and displaying a summary of the medical event score via the VR headset or a display screen.

This aspect can have a variety of embodiments. In one embodiment, the method can further include generating a virtual action implemented by a virtual character in the VR training environment based on at least one response received from the user. In another embodiment, the medical event further comprises a cardiac emergency event. In another embodiment, the method can further include converting at least one verbal response received from the user into text via a text-to-speech-application.

In another embodiment, the method can further include comparing the set of verbal responses to a set of medical guidelines, wherein the medical event score is further based on the comparison. In some cases, the set of medical guidelines further includes American Heart Association cardiac arrest guidelines.

In one embodiment, the method can further include updating a condition of a virtual patient based on at least one received verbal response. In some cases, the VR medical training environment further includes an in hospital cardiac arrest (IHCA) setting or an out of hospital cardiac arrest (OHCS) setting In one aspect, a VR headset can be adapted or configured to display a cardiac emergency event, receive, from a user, a set of verbal responses corresponding to the user reacting to the cardiac emergency event, determine a timestamp for at least one verbal response, determine a medical event score for the user based on the set of verbal responses and the timestamp, and display a summary of the medical event score.

This aspect can include a variety of embodiments. In one embodiment, the VR headset can be further adapted or configured to generate a virtual action implemented by a virtual character in the VR training environment based on at least one response received from the user. In some cases, the medical event includes a cardiac emergency event.

In one embodiment, the VR headset can be further adapted or configured to convert at least one verbal response received from the user into text via a text-to-speech-application. In one embodiment, the VR headset can be further adapted or configured to compare the set of verbal responses to a set of medical guidelines, where the medical event score is further based on the comparison. In some cases, the set of medical guidelines further comprises American Heart Association cardiac arrest guidelines.

In some cases, the VR headset is further adapted or configured to update a condition of a virtual patient based on at least one received verbal response. In some cases, the VR medical training environment further includes an in hospital cardiac arrest (IHCA) setting or an out of hospital cardiac arrest (OHCS) setting.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

A virtual reality (VR) system for medical training and associated methods are described herein. In some embodiments, the system may include a VR headset that generates and displays a medical event, such as a virtual patient experiencing a cardiac arrest. The user of the VR headset may be positioned as a team leader of a group of virtual medical professionals, where the user is tasked with leading and coordinating the group of virtual medical professionals. The virtual patient may exhibit symptoms related to a cardiac arrest, and the group of virtual medical professionals may include abilities of performing certain medical acts on the virtual patient and according to instructions provided by the user. The user may be scored based on his or her interactions with the group of virtual medical professionals and the virtual patient.

Figure 1:
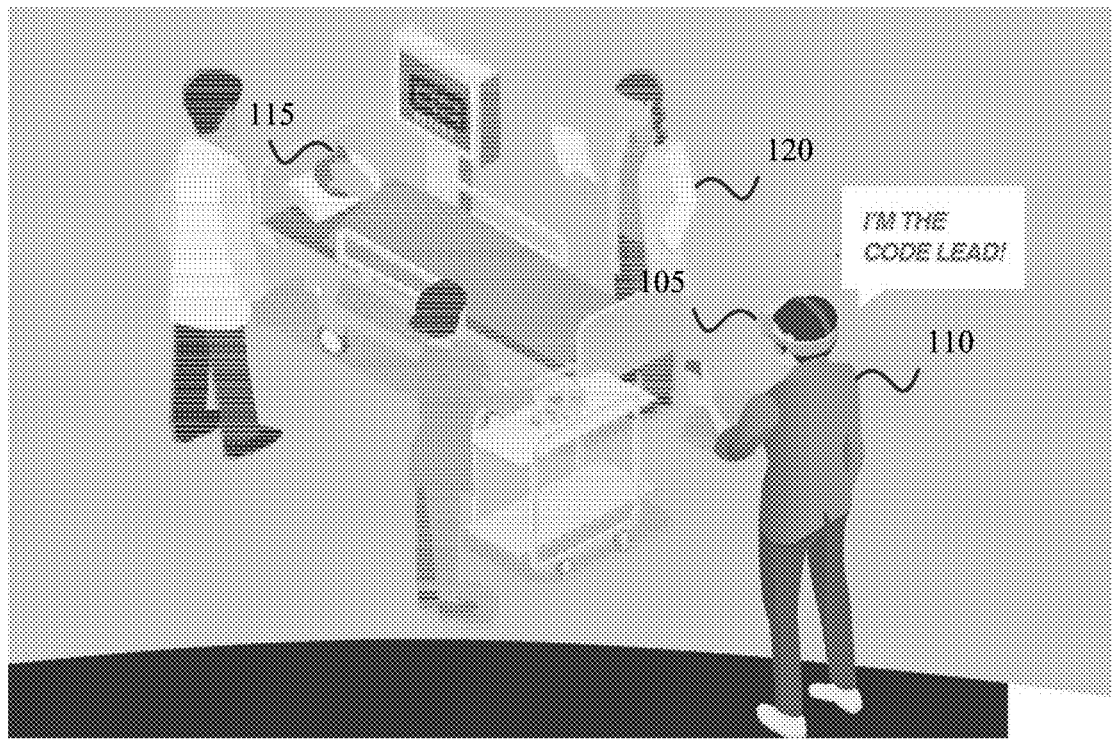
FIG. 1 depicts a system for virtual medical event training in accordance with embodiments of the claimed invention.

FIG. 1 depicts a system 100 for VR medical training, according to the claimed invention. The system may include a VR headset 105. The VR headset may be worn by a user, such as user 110. The VR headset may also generate and display a medical training scenario. The medical training scenario may include a virtual patient 115 and a group of virtual medical professionals 120. The virtual patient 115 may be experiencing a medical event, such as a cardiac arrest. However, it should be noted that the medical event may be a variety of medical conditions, such as a stroke, asphyxiation, a wound, an allergic reaction, etc.

The group of virtual medical professionals 120 may include a variety of medical professionals, including emergency medical technicians (EMTs), registered nurses (RNs), medical physicians, and the like. In some medical event scenarios, the group of medical professionals 120 may also include medical laymen, such as friends or passersby near the virtual patient 115. The user 110 may provide verbal instructions to the group of medical professionals or provide verbal observations related to the condition of the virtual patient 115. In some cases, the user 110 may receive visual indications for the user 110 to provide a verbal response. For example, the user 110 may receive a visual prompt from the VR headset screen, requesting that the user 110 provide an observation or instruction. In some cases, the prompt may be an audio prompt through the VR headset speakers.

The user 110 may provide a verbal response, which may be converted to text through a Text-to-Speech platform. Based on the user's response, the system may generate a "reaction" in the virtual environment. For example, if the user 110 provides a verbal instruction to a virtual medical professional 120, the system may generate the virtual medical professional 120 to follow the instruction of the user 110 and perform a medical act on the virtual patient 115. This may in turn provide additional information to the user 110, such as a virtual display of an additional effect on the virtual patient 115 (e.g., the patient is recovering), or may generate a new prompt for a user response.

Figure 2:
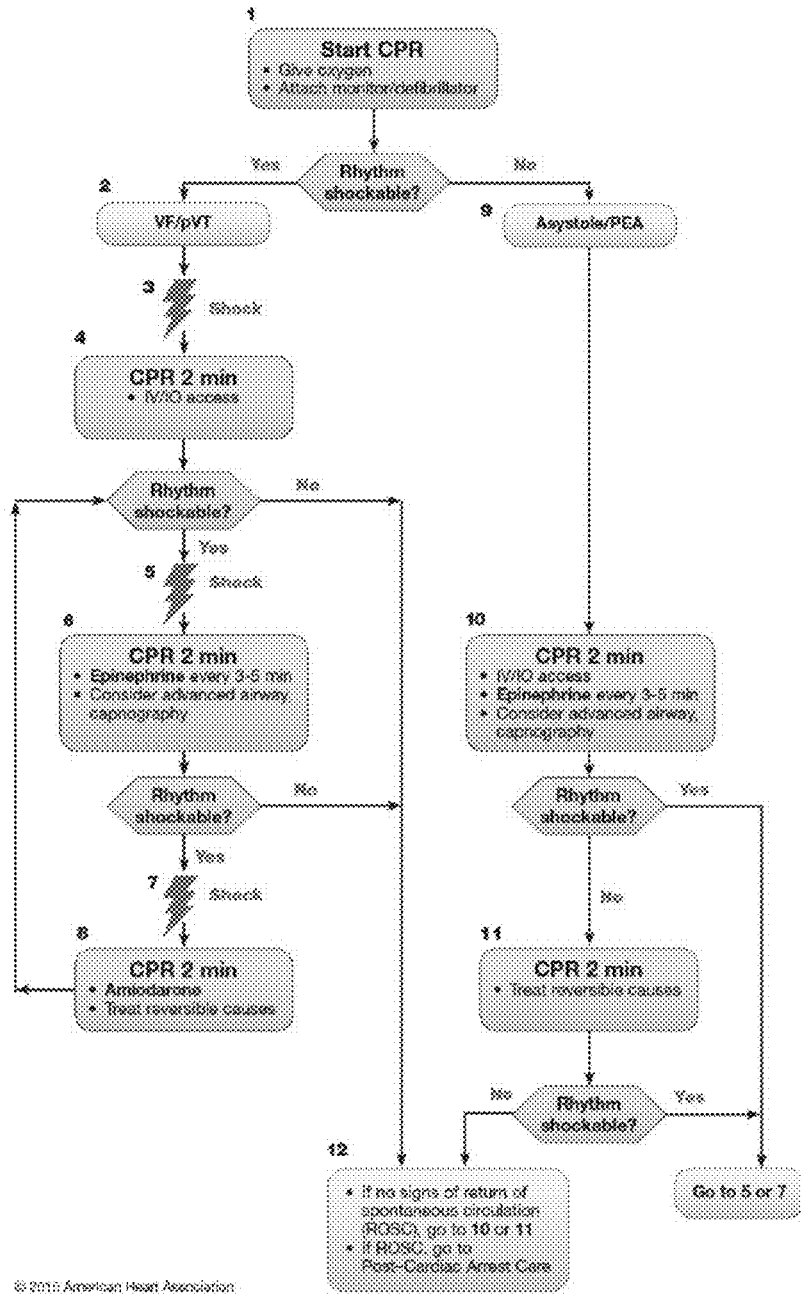
FIG. 2 depicts a decision workflow for mitigating a medical event in accordance with embodiments of the claimed invention.

The user 110 may be scored based on the user's provided instructions to the virtual group of medical professionals 120 as well as the observations of the virtual patient 115. For example, the user's instructions and observations may be compared to a predefined standard for the medical event. In the case of a cardiac arrest, the user's instructions and observations may be compared to Advanced Cardiac Life Support (ACLS) recommended actions. FIG. 2 illustrates a decision flow 200 for recommended actions for a user of the VR headset according to embodiments of the claimed invention. If a user instruction or observation deviates away from the recommended actions, the user's score may be lowered. As guidelines change and evolve over time, the system may be updated to reflect the changes in guidelines. For example, particular events in the decision flow 200 may closely align with ACLS recommended actions. The system may implement a Speech-to-Text platform in order to identify or determine the user's instructions.

The virtual patient 115 may exhibit symptoms of a medical condition in accordance with the training environment provided. For example, with a cardiac arrest event, the virtual patient may be depicted as unconscious and not breathing. Additionally, different medical acts conducted by the group of virtual medical professionals may alter the condition of the virtual patient 115 or may provide additional information for the user 110. For example, if the user 110 directs a virtual medical professional 120 to check the patient's heartbeat, the user 110 may be provided with a soundbite of a heartbeat. The user 110 may then be prompted to answer a question of whether this heartbeat is shockable or not.

Additionally, a user's time may be tracked and taken into account when a score is determined. For example, certain actions, such as chest compressions, may be recommended to occur for a predefined time period (e.g., 2 minutes at a time). The system may log the time inputted by the user 110 for a specific action related to the medical event. If the user 110 deviates from the predefined time period, the system may lower the score of the user 110.

Additionally or alternatively, the system may log timestamps for each individual response provided by the user 110. The system may determine times between responses (e.g., subtracting the timestamp from a second response from the timestamp from a third response) to determine timing metrics associated with the responses. Following the above example, the user 110 may direct a virtual medical professional 120 to begin chest compressions on the virtual patient 115. An action subsequent to the beginning of chest compressions and included in the underlying medical recommendations may be for a rhythm strip to be placed on the virtual patient. The underlying recommendations may list a predefined time period after the prior medical action for the subsequent medical action to occur. If the subsequent medical action is directed by the user, the system may log the time the instruction is received by the user. The system may determine whether the subsequent medical instruction is provided at the predefined time period. If the subsequent medical instruction time period deviates from the predefined time period, the system may alter the score of the user 110.

The scenario generated by the VR headset may vary based on user preferences and/or skill. In some cases, the VR headset may generate a "beginner-level" course for the user 110. This course may involve additional assistance from the system, such as questions or observations from the group of virtual medical professionals 120. For example, the user 110 may be prompted with questions for a specific medical act, such as "should we search for an AED?" If the user incorrectly responds with "no," the system may prompt the user 110 with a hint indicating that the user may wish to rethink the decision. Other scenarios may remove this generated additional assistance, for example in courses that are more advanced or if the user 110 selects a mode with limited or no assistance. Further, the generated scenarios may include situations where the user 110 is in a virtual in-hospital setting, such as in a hospital cardiac arrest (IHCA) setting, or a virtual out-of-hospital setting, such as an out of hospital cardiac arrest (OHCA) setting.

The user 110 may receive feedback at the conclusion of the virtual training program. The user feedback may include the score generated based on the user's instructions and observations during the virtual training event. The feedback may also include specific points of deficiency in relation to the underlying guidelines for the specific medical event that occurred. For example, the user 110 directs the group of medical professionals 120 to not shock the virtual patient 115, but the relevant guidelines recommend the user to instead direct the group of virtual medical professionals to shock the virtual patient. The feedback provided by the system may include this deviation, and may also provide recommendations to remedying the deviation. The feedback may be displayed on either the VR headset or on a display screen.

Figure 3:
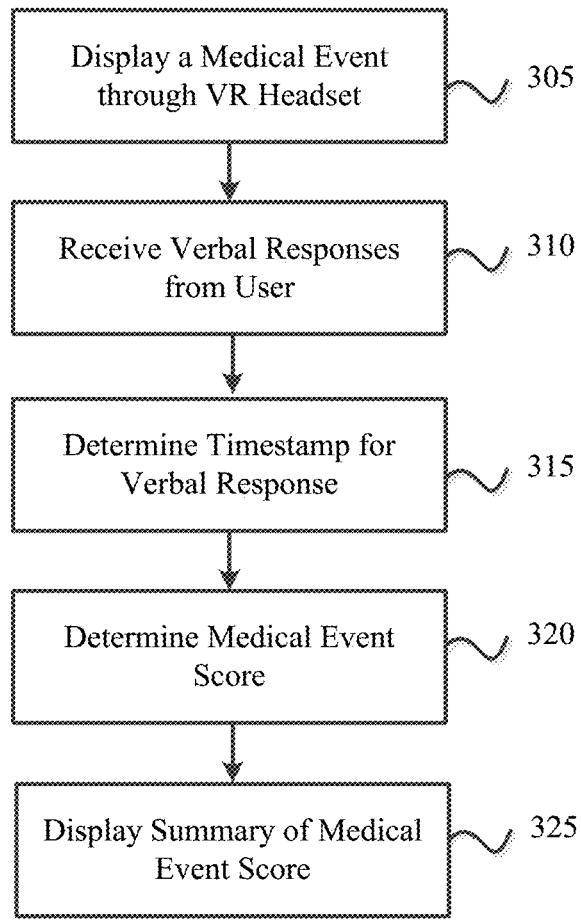
FIG. 3 depicts a process workflow for VR training for medical events in accordance with embodiments of the claimed invention.

FIG. 3 depicts a process workflow 300 for VR training for medical events in accordance with embodiments of the claimed invention. The process workflow may be implemented by a VR system, such as system 100 as described with reference to FIG. 1.

At Step 305, a medical event may be displayed through a VR headset. In some cases, the medical event may include a cardiac arrest of a virtual patient. At Step 310, a set of verbal responses may be received from a user of the VR headset. The set of verbal responses may correspond to the user reacting to the medical event. At Step 315, a timestamp for at least one verbal response received from the user may be determined.

At Step 320, a medical event score may be determined for the user based on the set of verbal responses and the timestamp. At Step 325, a summary of the medical event score may be displayed via the VR headset or a display screen.

The above-described steps can be implemented using standard well-known programming techniques. The novelty of the above-described embodiment lies not in the specific programming techniques but in the use of the steps described to achieve the described results. Software programming code which embodies the present invention is typically stored in permanent storage. In a client/server environment, such software programming code may be stored with storage associated with a server. The software programming code may be embodied on any of a variety of known media for use with a data processing system, such as a diskette, or hard drive, or CD ROM. The code may be distributed on such media, or may be distributed to users from the memory or storage of one computer system over a network of some type to other computer systems for use by users of such other systems. The techniques and methods for embodying software program code on physical media and/or distributing software code via networks are well known and will not be further discussed herein.

It will be understood that each element of the illustrations, and combinations of elements in the illustrations, can be implemented by general and/or special purpose hardware-based systems that perform the specified functions or steps, or by combinations of general and/or special-purpose hardware and computer instructions.

These program instructions may be provided to a processor to produce a machine, such that the instructions that execute on the processor create means for implementing the functions specified in the illustrations. The computer program instructions may be executed by a processor to cause a series of operational steps to be performed by the processor to produce a computer-implemented process such that the instructions that execute on the processor provide steps for implementing the functions specified in the illustrations. Accordingly, the figures support combinations of means for performing the specified functions, combinations of steps for performing the specified functions, and program instruction means for performing the specified functions.

While there has been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method for generating a virtual reality (VR) medical training environment, the method comprising:
 displaying a virtual reality medical event through a VR headset;
 receiving, from a user of the VR headset, a set of verbal responses corresponding to the user reacting to the virtual reality medical event;
 determining a timestamp for at least one verbal response received from the user;
 determining a medical event score for the user based on the set of verbal responses and the timestamp, the medical event score being based on a comparison of the set of verbal responses to a set of predetermined medical guidelines; and
 displaying a summary of the medical event score via the VR headset or a display screen.

2. The method of claim 1, further comprising:
 generating a virtual action implemented by a virtual character in the VR training environment based on at least one response received from the user.

3. The method of claim 1, wherein the medical event further comprises a cardiac emergency event.

4. The method of claim 1, further comprising:
 converting at least one verbal response received from the user into text via a text-to-speech-application.

5. The method of claim 1, wherein the set of medical guidelines comprises American Heart Association cardiac arrest guidelines.

6. The method of claim 1, further comprising:
 updating a condition of a virtual patient based on at least one received verbal response.

7. The method of claim 1, wherein the VR medical training environment further comprises an in hospital cardiac arrest (IHCA) setting or an out of hospital cardiac arrest (OHCS) setting.

8. A system for generating a virtual reality (VR) medical training environment, the system comprising:
 a VR headset adapted or configured to:
 display a virtual reality cardiac emergency event;
 receive, from a user, a set of verbal responses corresponding to the user reacting to the virtual reality cardiac emergency event;
 determine a timestamp for at least one verbal response;
 determine a medical event score for the user based on the set of verbal responses and the timestamp, the medical event score being based on a comparison of the set of verbal responses to a set of predetermined medical guidelines; and
 display a summary of the medical event score.

9. The system of claim 8, wherein the VR headset is further adapted or configured to:
 generate a virtual action implemented by a virtual character in the VR training environment based on at least one response received from the user.

10. The system of claim 8, wherein the VR headset is further adapted or configured to:
 convert at least one verbal response received from the user into text via a text-to-speech-application.

11. The system of claim 8, wherein the set of medical guidelines further comprises American Heart Association cardiac arrest guidelines.

12. The system of claim 8, wherein the VR headset is further adapted or configured to:
 update a condition of a virtual patient based on at least one received verbal response.

13. The system of claim 8, wherein the VR medical training environment further comprises an in hospital cardiac arrest (IHCA) setting or an out of hospital cardiac arrest (OHCS) setting.

* * * * *